United States Patent [19]

Drago et al.

[11] Patent Number: 5,186,899
[45] Date of Patent: Feb. 16, 1993

[54] FIXTURE FOR SUPPORTING A REFRIGERANT SAMPLING TUBE IN A CLOSED SYSTEM

[76] Inventors: Thomas E. Drago, 4775 Black Oak Dr., Liverpool, N.Y. 13088; Alan D. Abbott, 4470 Brickyard Falls Rd., Manlius, N.Y. 13104

[21] Appl. No.: 612,639

[22] Filed: Nov. 13, 1990

[51] Int. Cl.$^5$ .............................................. G01N 1/22
[52] U.S. Cl. ..................................... 422/104; 422/58; 422/86; 422/88
[58] Field of Search ............... 422/86, 88, 104, 102, 422/58; 436/39; 73/864.91, 864.73, 864.33; 269/70, 254 CS, 254 R; 285/24, 27, 31, 114, 9.2; 366/208

[56] References Cited

U.S. PATENT DOCUMENTS

| | | | |
|---|---|---|---|
| 1,284,160 | 9/1917 | Simpson | 285/114 |
| 1,632,718 | 8/1926 | Wallace | 366/208 |
| 4,046,015 | 9/1977 | Riedl et al. | 73/864.91 |
| 4,159,304 | 6/1979 | Shono | 422/104 |
| 4,389,372 | 6/1983 | Lalin | 422/86 |
| 4,769,281 | 9/1988 | Leichnitz et al. | 422/86 |
| 4,923,806 | 5/1990 | Klodowski | 436/39 |

Primary Examiner—James C. Housel
Assistant Examiner—Long V. Le

[57] ABSTRACT

A holder for use with a refrigerant purity sampling tube is provided with a base and two end fittings. The end fittings are adapted to establish a releasably fluid tight relationship with the opposite ends of a sampling tube. One end fitting is fixed to the base and the other is slideably mounted for movement toward and away from the fixed fitting. A spring biases the movable end fitting toward a fixed fitting. Movement of the movable fitting against the biasing force allows removal and insertion of a sampling tube. When a new tube is inserted, the biasing force assures fluid tight engagement with the seal.

5 Claims, 2 Drawing Sheets

FIXTURE FOR SUPPORTING A REFRIGERANT SAMPLING TUBE IN A CLOSED SYSTEM

BACKGROUND OF THE INVENTION

1. Field of the Invention

The present invention relates to a support fixture for supporting a refrigerant sampling tube in a closed loop refrigeration circuit.

2. Description of the Prior Art

Recently systems have been developed which allow sampling of air or other gaseous compositions such as refrigerants in order to detect the presence of impurities therein. Such systems utilize gas detection tubes filled with various chemical reagant materials for detecting such impurities and contamination. The detection or sampling tubes are typically used in combination with a pump for drawing the gaseous composition being tested through the tubes at a predetermined flow rate to provide an indication of the presence of impurities as well as to provide a measure of the concentration of the impurity over a given test sampling time.

Most gas detection tubes are designed in the form of an elongated cylindrical enclosure of transparent material such as pyrex glass into which the indicating reagent materials are placed before the opposite ends are drawn and sealed.

U.S. Pat. No. 4,923,806 entitled Method and Apparatus for Refrigerant Testing in a Closed System is assigned to the assignee of the present invention and is directed to a method and apparatus for detecting contaminants in a refrigerant medium. This patent teaches the use of single use transparent glass testing tubes which are sealed until used and which contain therein an oil removal section, a water removal and indicating section and an acid indicating section. In use the ends of the glass testing tube are broken off and the tube is placed in a tube holder apparatus which functions to seal the tube so that all the refrigerant flow is directed through the tube. The presence of contaminants is indicated by a color change which may be quantified by comparison to a color chart and/or the extent of the promulgation of the color change in the indicating media.

The holder for the sampling tube disclosed in the '806 patent is adapted to allow a flow of refrigerant to be tested to pass therethrough and then vents it to the atmosphere. The venting of refrigerant gas to the atmosphere is not considered to be an environmentally acceptable expedient.

Other holder devices for gas detection tubes are shown and described in U.S. Pat. No. 4,159,304 Portable Gas Detection Tube Holder and U.S. Pat. No. 4,389,372 Portable Holder Assembly for Gas Detection Tube. Both of the above cited patents incorporate threaded fittings which must be disassembled in order to change the sampling tube contained therein.

A refrigerant purity sampling arrangement has recently been developed wherein a refrigerant puriity sampling tube is mounted in a parallel fluid flow relationship with a refrigerant compressor which operates to provide a pressure differential which provides the necessary fluid flow through the sampling tube to test the purity of refrigerant in the refrigeration system of which the compressor forms a part. This testing system forms the subject matter of a separate United States patent application entitled Method and Apparatus For Sampling the purity of refrigerant flowing through a refrigeration circuit which is assigned to the assignee of the present application and is filed on even date herewith.

SUMMARY OF THE INVENTION

It is an object of the present invention to provide a fixture for supporting a refrigerant sampling tube which is mounted in a high pressure system across the suction and discharge of a compressor without purging refrigerant to the atmosphere.

A further object is to provide a device for holding a sampling tube that effects a leak proof path for the gas flowed therethrough in a high pressure system.

Another object of the invention is to provide a device for holding a sampling tube that allows quick, simple insertion and removal of the tube from the holder.

These and other objects of the present invention are achieved by providing a holder for use with a sampling tube of the type through which a fluid to be tested is passed. The holder includes a mounting base having a pair of end fittings mounted thereon. Both end fittings include means for releasably engaging one end of a sampling tube and for establishing a fluid tight fluid path with the interior of the tube. Each end fitting also includes means for establishing a fluid communication between the means for releasably engaging and an external conduit. One of the end fittings is fixed with respect to the base and the other end fitting is slidably mounted on the base for movement toward and away from the fixed end fitting. The end fittings are oriented such that the means for releasably engaging the ends of the sampling tube are in spaced confronting relationship with one another and means are provided for biasing the slidably mounted end fitting toward the fixed end fitting.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of the preferred embodiment when read in connection with the accompanying drawings wherein:

DESCRIPTION OF THE PREFERRED EMBODIMENT

Figure 1:
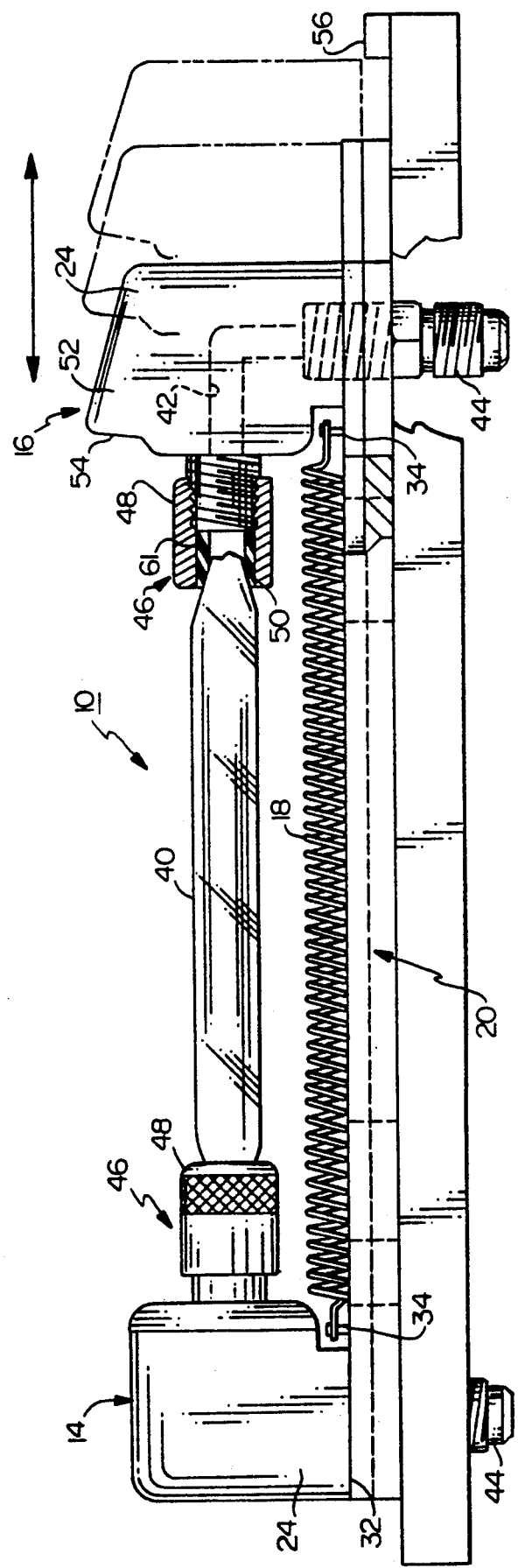
FIG. 1 is a side view of the sampling tube holder assembly of the present invention.
Figure 2:
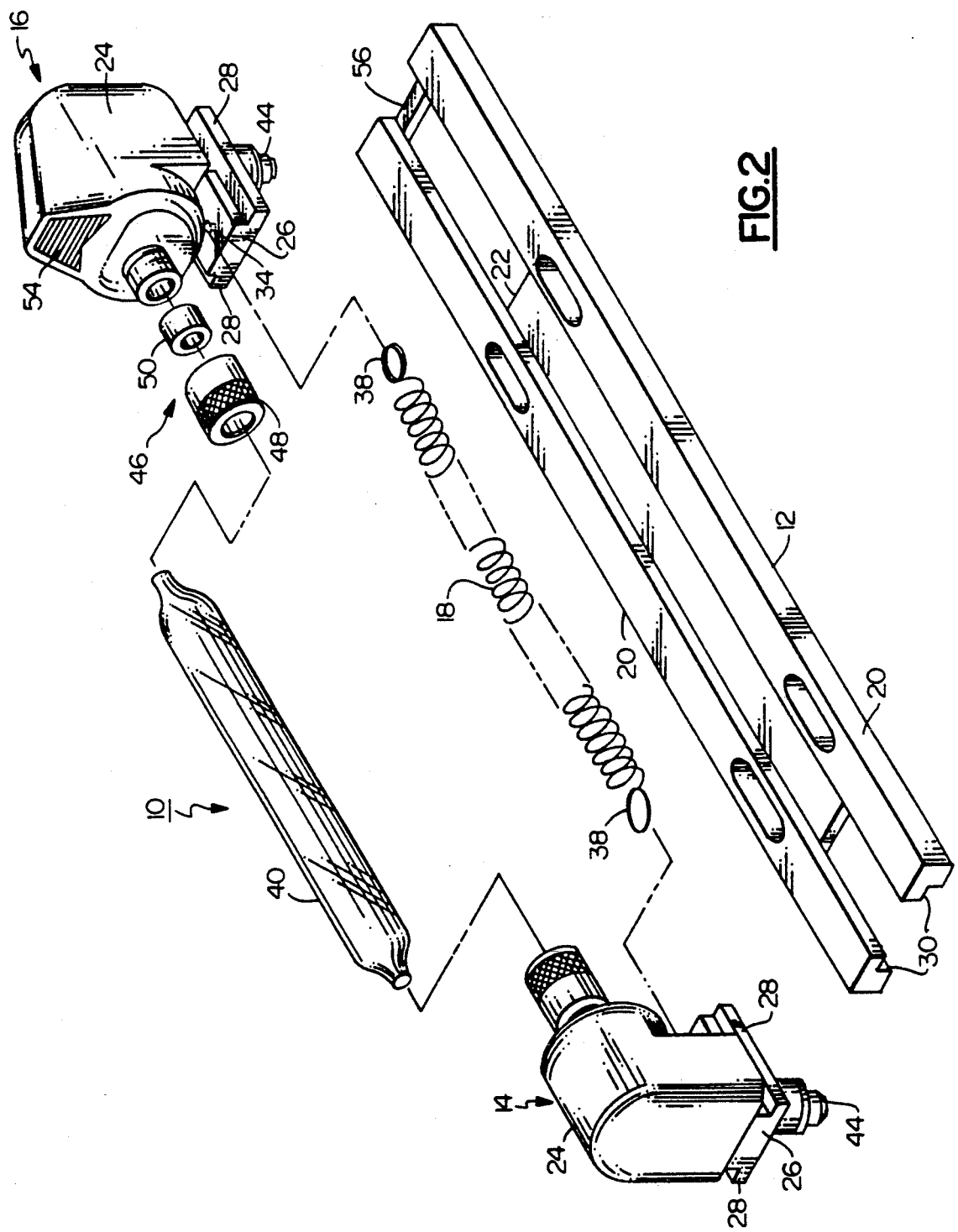
FIG. 2 is a perspective exploded view of the sampling tube holding fixture of the present invention.

Referring now to both of the drawing figures the sampling tube support fixture 10 of the present invention includes a supporting base 12, a fixed end fitting 14, a movable end fitting 16, and, an interconnecting biasing spring 18.

The structure of the base 12 takes on the appearance of a rail in that it comprises two parallel extending, inverted L shaped sections 20 which one interconnected by a central web like portion 22 which is shorter than the section 20. The base essentially defines an elongated H shape as viewed from the top with the legs being longer at the right hand end of the base upon which the moveable end fitting 16 is mounted. Four elongated mounting slots 24 are provided, two in each rail, to facilitate ease of mounting of the fixture.

The end fittings 14 and 16 are substantially identical each having a main body portion 24 and a mounting portion 26 which extends from the lower end of the body and defines an inverted T shaped cross section. The two laterally extending legs 28 of the mounting portion are adapted to be received in sliding relationship with mating channel like surfaces 30 defined by the inverted L shaped portions of the legs forming the ends of the base 12. The lower surface 32 of the main body portion rests on the top of the rails 20. The fixed end fitting 14 is appropriately fastened to the base 12 for example by a suitable adhesive.

The moveable end fitting 16 is slideably received in the end of the base 12 having the longer legs and as will be seen is moveable axially with respect to the base as depicted in FIG. 1. Each of the end fittings 14 and 16 is provided with a spring anchor device 34 mounted on the upper side of the T shaped mounting extension 26. The longitudinally extending tension spring 18 having suitable anchoring loops 38 at each end engages the anchor devices 34 of both the fixed and moveable end fittings. The length of the spring is such that when anchored to both end fittings 14, 16 as depicted in FIG. 1 a substantial force is exerted on the moveable end fitting to the left. This force is critical to obtaining and maintaining the seal between the fixture and the sampling tube 40 mounted therein as will be appreciated as the engagement of the end fittings 14 and 16 with the sampling tube is described.

Each of the end fittings 14 and 16 has a flow path defined therethrough which includes an internal channel 42 interconnected by a pair of threaded fittings. A first threaded flow fitting 44 is mounted to the mounting extension 26. In the illustrated embodiment each of the fittings 44 is provided with a standard ¼ inch flare fitting to facilitate attachment to appropriate flow conduits in a testing system.

A second set of fittings 46 which define the sampling tube support and seal configuration are mounted in the bodies 24 of the end fittings 14 and 16 such that they are in confronting axially aligned relationship with one another when the device is assembled. Each of the fittings 46 defines a standard ¼ inch flare fitting upon which a ¼ inch flare cap 48 with a ¼ inch diameter hole drilled therein is threadably engaged. A cylindrical rubber seal 50 is disposed within each of the flare caps 48 as shown in the broken away view of the seal arrangement on the moveable end fitting 16 in FIG. 1.

The seal 50 is inserted into the flare cap 48, prior to assembly of the cap to flare fitting, through the opening adjacent to the threaded end. When the cap 48 is threaded into the fitting the seal is retained between the fitting and an annular lip 51 formed at the end of the flare cap 48.

As thus described a sample tube 40 is installed within the fixture 10 by first breaking off ends of the glass sample tube, pulling back the moveable end fitting 16 an appropriate distance to allow one end of the sampling tube to be inserted into engagement with the seal fitting 46 of the fixed end fitting 14, and, while holding the tube in proper alignment, allowing the moveable fixture 16 to move, under the force of the spring, into appropriate sealing engagement with the other end of the sampling tube. As thus installed the flare fittings and the seal elements 50 inside the flare cap 48, in combination with the constant tension provided by the spring, establish a leak proof path through the fixture.

In the preferred embodiment the spring is selected to maintain a constant five pounds of tension against the seals 50 which will allow a pressure maximum of over 200 psi before leakage occurs around the seal. It should be appreciated that the rubber seals may, with continued use, lose their sealing integrity as they are subject to damage by the rough ends of the sampling tube 40. The seals 50 may be readily removed and replaced with new ones as the flare caps may be unscrewed by hand and a new rubber seal installed as necessary.

Looking now to FIG. 1 the upper portion of the body 24 of the moveable end fitting 16 is provided with an angularly disposed upward extension 52 which defines a textured surface 54 facing to the left as viewed in the drawing figure. This surface is adapted to be engaged by an operators thumb while the other fingers of the hand engage an appropriate structure 56 provided in an ergonomically comfortable location to facilitate moving the movable end fitting 16 against the force of the spring 36.

It should accordingly be appreciated that a fixture for supporting a refrigerant sampling tube in a closed loop across the high and low side of a compressor has been provided. The device will hold the sampling tube in a leak proof path allowing flow of the gas to be sampled therethrough from an inlet to an outlet both connected into a circuit of the refrigeration system. The device achieves all of the above while allowing a quick simple insertion and removal of sampling tubes from the device.

This invention may be practiced or embodied in still other ways without departing from the spirit or central character thereof. The preferred embodiment described herein is therefore illustrative and not restrictive. The scope of the invention being indicated by the appended claims and al variations which come within the meaning of the claims are intended to be embraced therein.

We claim:

1. A holder for use with a sampling tube of the type through which a fluid to be tested is passed, comprising;
   a base;
   a first end fitting including:
   means for releasably engaging one end of a sampling tube, and, for establishing a fluid tight, fluid path with the interior of the tube; and
   means for establishing fluid communication between said means for releasably engaging, and, an external conduit;
   said first end fitting being fixedly attached to said base;
   a second end fitting including:
   means for releasably engaging the other end of a sampling tube and for establishing a fluid tight fluid path with the interior of the tube; and
   means for establishing fluid communication between said means for releasably engaging and an external conduit;
   said second end fitting being slidably mounted on said base, for movement toward and away from said first end fitting, with said means for releasably engaging being in spaced confronting relationship with said means for releasably engaging of said first end fitting; and
   means for biasing said slidably mounted second end fitting toward said first end fitting.

2. The apparatus of claim 1 wherein said means for biasing comprises a coil spring connected at opposite ends thereof to said first and second end fittings.

3. The apparatus of claim 1 wherein said means for releasably engaging and establishing a fluid tight seal comprises:
- a cylindrical element having oppositely disposed open ends; and
- an annular seal element coaxially received in one open end of said cylindrical element,
- said seal having an internal diameter adapted to sealingly engage the outer surface of a sampling tube inserted into said one open end.

4. The apparatus of claim 3 wherein each of said end fittings includes a body; said means for establishing fluid communication comprises:
- a first fitting mounted on a surface of said body for engaging said other end of said cylindrical element;
- a second fitting mounted on another surface of said body; and
- a passage within said body for establishing fluid communication between said first and second fittings.

5. The apparatus of claim 4 wherein said first fitting comprises a threaded flare fitting, and, said cylindrical element comprises a flare cap having an opening formed in said normally closed end to adapt to the size of the sampling tube to be used with said holder.

* * * * *